US012779119B2

United States Patent
(12) Navara et al.

(10) Patent No.: US 12,779,119 B2
(45) Date of Patent: Nov. 3, 2026

(54) SYSTEM FOR REMOTE DRUG MONITORING AND TITRATION

(71) Applicant: SAFEBEAT RX INC., Carson, CA (US)

(72) Inventors: Rachita Navara, Manteca, CA (US); Kunj G. Patel, Manteca, CA (US)

(73) Assignee: SAFEBEAT RX INC., Carson, CA (US)

( * ) Notice: Subject to any disclaimer, the term of this patent is extended or adjusted under 35 U.S.C. 154(b) by 470 days.

(21) Appl. No.: 18/286,116

(22) PCT Filed: Apr. 23, 2022

(86) PCT No.: PCT/US2022/026069

§ 371 (c)(1),
(2) Date: Oct. 7, 2023

(87) PCT Pub. No.: WO2022/231988

PCT Pub. Date: Nov. 3, 2022

(65) Prior Publication Data

US 2025/0082848 A1 Mar. 13, 2025

Related U.S. Application Data

(60) Provisional application No. 63/270,383, filed on Oct. 21, 2021, provisional application No. 63/179,499, filed on Apr. 25, 2021.

(51) Int. Cl.
*A61M 5/172* (2006.01)
*A61N 1/39* (2006.01)
(Continued)

(52) U.S. Cl.
CPC ......... *A61M 5/1723* (2013.01); *A61N 1/3968* (2013.01); *G16H 20/10* (2018.01);
(Continued)

(58) Field of Classification Search
CPC .......... A61M 5/1723; A61M 2205/502; A61M 2230/06; A61N 1/3968; G16H 20/10;
(Continued)

(56) References Cited

U.S. PATENT DOCUMENTS

2011/0092838 A1* 4/2011 Helfenbein .............. A61B 5/36 600/516
2012/0265556 A1* 10/2012 Lebovitz ........... A61M 5/14276 705/2

(Continued)

FOREIGN PATENT DOCUMENTS

WO 2014176529 10/2014
WO WO-2014176529 A2 * 10/2014 ................ A61P 9/00

OTHER PUBLICATIONS

International Search Report dated Nov. 3, 2022 from corresponding PCT application No. PCT/US2022/26069.

(Continued)

*Primary Examiner* — Lauren P Farrar

(57) ABSTRACT

Provided here is an apparatus, a computer program product, and a method for providing a corrected QT interval (QTc) measurement from electrocardiographic data. The method comprises step of receiving electrocardiographic data from at least one electrocardiogram (ECG) source; cleansing said electrocardiographic data; extracting ECG segments from cleansed electrocardiographic data based on ECG channel electrode(s) of interest; providing one or more baseline models trained with annotated segments to generate interpreted heart rhythm/rate based on the extracted ECG segments; selecting an image processing model based on the interpreted heart rhythm/rate; and applying the selected image processing model to the cleansed electrocardiographic data, where the image processing model outputs the QTc measurement.

20 Claims, 7 Drawing Sheets

(51) Int. Cl.

| | |
|---|---|
| ***G16H 20/10*** | (2018.01) |
| ***G16H 30/40*** | (2018.01) |
| ***G16H 40/67*** | (2018.01) |

(52) U.S. Cl.
CPC ............. *G16H 30/40* (2018.01); *G16H 40/67* (2018.01); *A61M 2205/502* (2013.01); *A61M 2230/06* (2013.01)

(58) Field of Classification Search
CPC ........ G16H 30/40; G16H 40/67; G16H 40/63; G16H 50/20; G16H 50/30; G16H 50/70; A61B 5/4839; A61B 5/36
See application file for complete search history.

(56) References Cited

U.S. PATENT DOCUMENTS

| | | | | |
|---|---|---|---|---|
| 2015/0088017 | A1 | 3/2015 | Farazi | |
| 2019/0380605 | A1 | 12/2019 | Ivaturi et al. | |
| 2021/0027891 | A1 * | 1/2021 | Rajput | G16H 70/40 |

OTHER PUBLICATIONS

Written Opinion of the International Searching Authority dated Nov. 3, 2022 from corresponding PCT application No. PCT/US2022/26069.

* cited by examiner

SYSTEM FOR REMOTE DRUG MONITORING AND TITRATION

CROSS REFERENCE TO RELATED APPLICATIONS

This application claims the priority benefit of Provisional Application No. 63/270,383 filed on 21 Oct. 2021 and Provisional Application No. 63/179,499 filed on 25 Apr. 2021, the entire disclosures of which are incorporated herein by reference.

FIELD OF INTERVENTION

The present disclosure relates to a system for providing remote drug monitoring and titration in accordance with heart electrical rhythm data.

BACKGROUND

Atrial fibrillation (AF) is the most common arrhythmia affecting over 38 million people worldwide, with an annual incidence of 6 million cases. Available antiarrhythmic drugs (AADs) treat AF by restoring normal sinus rhythm and reducing symptoms. Clinical trial data has also shown decreased mortality and improved cardiovascular outcomes from rhythm control in AF patients. However, access to oral AADs is restricted by the required three-day hospitalization for initiation or even dose increase, due to a rare (<0.6%) but potentially life-threatening rhythm side effect, called Torsades de Pointes (TdP).

TdP is prevented by twice-daily electrocardiogram (ECG) review and measurement of the QTc interval on each ECG. For low-risk patients, the risks of hospitalization outweigh those of the medication. Mandatory (three-day) hospitalization for drug initiation is not only inconvenient for patients and the clinical team, but also significantly costly. Most isolated TdP cases (50-76%) happen in the first three days of drug initiation, but rhythm side effects can still occur beyond three days. This reveals the somewhat arbitrary three days duration, which ultimately does not change outcomes for most patients and leaves higher-risk patients unmonitored after discharge.

Though AADs were approved over two decades ago, there has been no alternative to hospitalization to initiate or dose-adjust these medications. There is an unmet need for a safe, all-encompassing solution for outpatient antiarrhythmic monitoring that is described herein.

SUMMARY

This Summary is provided to introduce a selection of concepts in a simplified form that are further described below in the Detailed Description. This Summary is not intended to identify key features or essential features of the claimed subject matter, nor is it intended to be used to determine the scope of the claimed subject matter; variants and alternative features which facilitate the working of the invention and/or to achieve a substantially similar technical effect should be considered as falling into the scope of the invention disclosed herein.

The present disclosure provides a new solution for safe mobile drug initiation centered on integrating a mobile ECG, mobile cardiac telemetry (MCT), and a wearable cardioverter defibrillator (WCD) with a novel software implementation. This is the first integration of mobile ECG and WCD hardware with automated ECG software to produce an all-encompassing mobile drug initiation and titration system, e.g. the SafeBeat Kit™. The novel software provides physicians with automated ECG analysis using time series analysis, image processing, and machine learning steps. The software is also configured to incorporate the clinical characteristics of a patient along with ECG analysis to provide personalized dose guidance remotely, as the first alternative to hospitalization.

In a first aspect, the present disclosure provides a method or a computer-implemented method for providing a corrected QT interval (QTc) measurement from electrocardiographic data, the method comprising: receiving electrocardiogram at least one ECG source; cleansing said electrocardiographic data; extracting ECG segments from cleansed electrocardiogram ECG channel electrode(s) of interest; providing one or more baseline models trained with annotated segments to generate interpreted heart rhythm/rate based on the extracted ECG segments, selecting an image processing model based on the interpreted heart rhythm/rate; and applying the selected image processing model to the cleansed electrocardiographic data, wherein the image processing model outputs the QTc measurement.

In a second aspect, the present disclosure provides an apparatus, comprising: at least one processor and a memory including computer program code, the memory and the computer program code configured to, with the at least one processor, cause the apparatus to perform the method of the first aspect.

Moreover, the novel ECG automation software is trained on over 13,000 heartbeats individually annotated and validated by cardiologists to ensure the quality of ECG analysis with high accuracy (5.2±7.2 ms), in order to meet the clinical standard of physician-overread hospital ECGs. The software comprises an interface module that permits closed-loop communication between the physician and patient to provide safe and effective dose guidance. The software also ensures that this communication is encrypted but auditable if required.

In a fourth aspect, the present disclosure provides an interactive remote drug dose guidance and physiologic response monitoring system for the patient, the system comprising: a first module configured to interface with the patient using a secured communication, wherein the first module is adapted to receive periodically, through the secured communication, ECG data from the patient for a predetermined time period ("drug load"); and a second module configured to generate one or more QTc measurements based on the periodically received ECG data and provide said one or more dosage recommendations in a sequential manner, within the predetermined time period, with each dosage recommendation provided based on said one or more QTc measurements.

In a fifth aspect, the present disclosure provides a system of the first aspect, wherein the second module is configured to cleanse the received ECG data; extract ECG segments from cleansed electrocardiographic data based on ECG channel electrode(s) of interest; provide one or more baseline models trained with annotated ECGs to generate interpreted heart rhythm/rate based on the extracted ECG segments; select an image or signal processing model based on the interpreted heart rhythm/rate and apply the selected image or signal processing model to the cleansed electrocardiographic data to generate the QTc measurement.

The methods described herein may be performed by software in machine-readable form on a tangible storage medium, e.g. in the form of a computer program comprising computer program code means adapted to perform all the steps of any of the methods described herein when the program is run on a computer and where the computer program may be embodied on a computer-readable medium. Examples of tangible (or non-transitory) storage media include disks, thumb drives, memory cards etc. and do not include propagated signals. The software may be suitable for execution on a parallel processor or a serial processor such that the method steps may be carried out in any suitable order, or simultaneously.

This application acknowledges that firmware and software may be valuable, separately tradable commodities. It is intended to encompass software, which runs on or controls "dumb" or standard hardware, to carry out the desired functions. It is also intended to encompass software which "describes" or defines the configuration of hardware, such as HDL, (hardware description language) software, as is used for designing silicon chips, or for configuring universal programmable chips, to carry out desired functions. The preferred or optional features may be combined as appropriate, as may be apparent to a skilled person, and may be combined with any of the aspects of the invention.

BRIEF DESCRIPTION OF THE DRAWINGS

Embodiments of the invention will be described, by way of example, with reference to the following drawings, in which.

DETAILED DESCRIPTION

Figure 1:
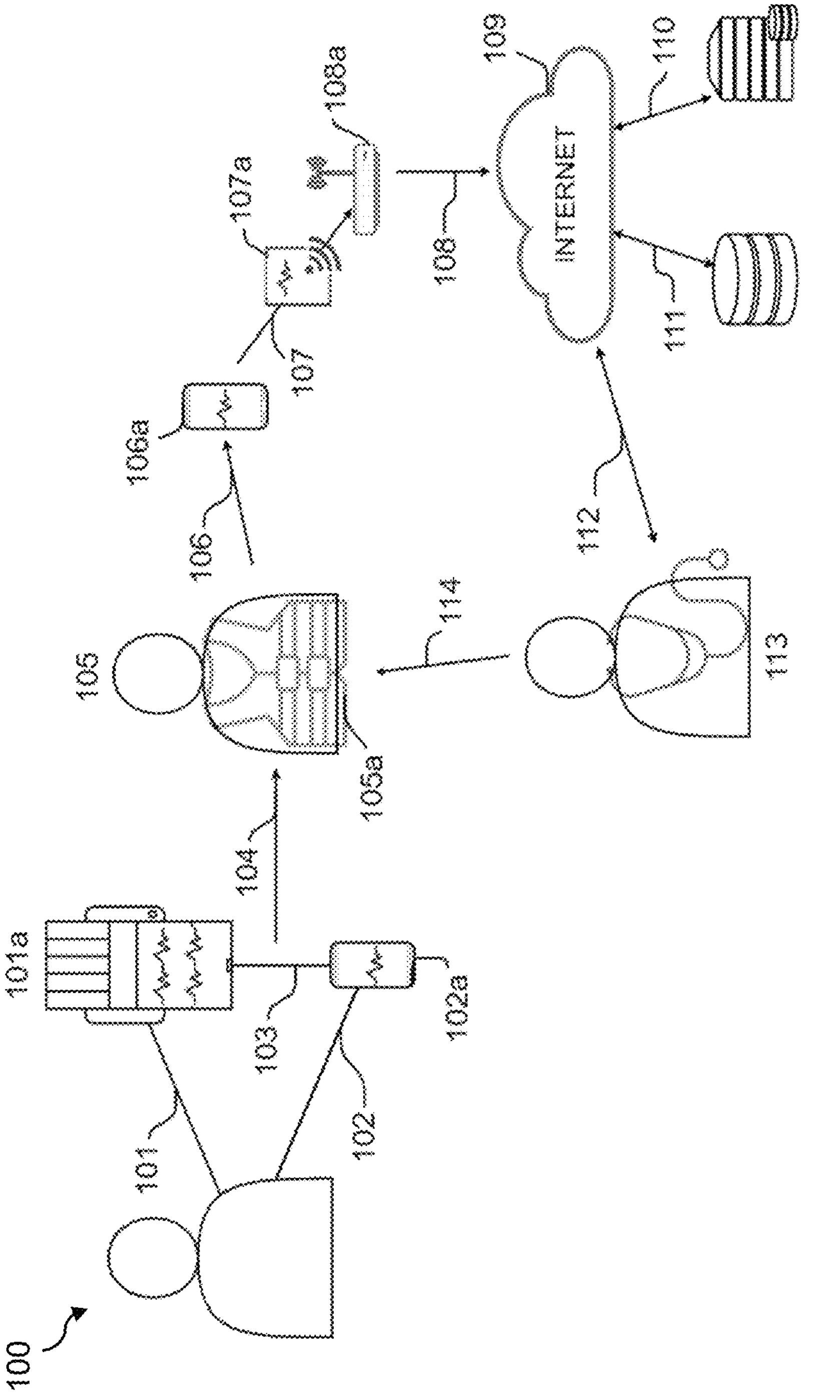
FIG. 1 is a block diagram illustrating an example system and computing devices suitable for implementing aspects of the invention.

Embodiments of the present invention are described below by way of example only. These examples represent the suitable modes of putting the invention into practice that are currently known to the Applicant, although they are not the only ways in which this could be achieved. The description sets forth the functions of the example and the sequence of steps for constructing and operating the example. However, the same or equivalent functions and sequences may be accomplished by different examples.

There is no commercially available competitor technology or product that offers an all-encompassing solution for outpatient antiarrhythmic monitoring such as this invention, which provides continuous safety, image-based and/or signal-based software that may automate QTc measurement from any ECG hardware device with or without raw or digitized input data, and data-driven dose guidance personalized to the patient.

There is no integrated system that employs the present invention specifically for home antiarrhythmic initiation. Generic hardware suitable for implementing the present invention exists. For example, the kit may contain the Zoll® LifeVest AED Plus®, or Kestra Medical Technologies ASSURE WCD, which are currently the only FDA-approved WCD devices. However, these vests do not support the measurement of QTc. The present disclosure does not limit the system to be adapted to or to incorporate an alternative defibrillator or safety device with QTc measurement.

As such, the present system, when applied with the alternative defibrillator types such as the implanted cardioverter defibrillator (ICD), WCD, and automated external defibrillator (AED), is adapted to utilize pulse sensor technologies, e.g. a photoplethysmogram (PPG) sensor, which allows for the detection of blood volume changes with each cardiac cycle, thus enabling accurate pulse detection. The inclusion of pulse sensor data, whether from a pulse sensor on the transvenous leads in an ICD system or from traditional external skin sensors for WCD and AED systems, will enable the defibrillator to distinguish between perfusing and pulseless arrhythmias.

In conjunction with the drug-monitoring system, the additional PPG input data will improve the accuracy of defibrillation for patients experiencing ventricular arrhythmias, with avoidance of inappropriate or premature shocks for perfusing rhythms. Accordingly, the adaptation of the present system with the defibrillators utilizing pulse sensor technology indeed improves the present use of defibrillators or defibrillation devices even independently of the drug monitoring system described herein.

Further, while there are many mobile ECG devices available, very few are FDA-cleared for manual QTc measurement (e.g. AliveCor® KardiaMobile 6L).

Therefore, there lacks a safe method for outpatient antiarrhythmic initiation, supported by automated mobile ECG analysis and continuous safety, especially via a defibrillator, e.g. a WCD. Moreover, no existing software solution incorporates clinical data to both automate QTc measurement and provide personalized dose guidance to maximize safety.

Compared to the software implementation in this invention, existing algorithms attempting to automate QTc have lower precision and/or sensitivity despite optimized input data. For example, a published QT algorithm (Giudicessi, John R., et al., 2021) based purely on machine learning (ML) was trained and tested on clean, digital ECGs in a population with normal HR and regular rhythm. Compared to a cardiologist, this algorithm achieved much lower sensitivity (50-64% for QTcF) when detecting QTc above the same cut-offs tested for this invention in Table 1 (90-91% sensitivity). Only 67% of their cases met the ECG standard (20 ms accuracy), compared to 98.5% using the software in this invention—the latter being tested on a much more challenging ECG dataset including long QT and AF ECGs.

One of many advantages reserved by receiving electrocardiogram at least one ECG source and cleansing said electrocardiographic data is to improve the overall data quality for extracting the extracting ECG segments from cleansed electrocardiographic data based on ECG channel electrode(s) of interest in an effective manner and suitable for use with one or more baseline model. From extracted ECG segments, the underlying code generates a more accurately interpreted heart rhythm/rate and provides detectability for further selection by the image or signal processing model. The QTc output is more accurate than existing methods.

Throughout this application, electrocardiographic data refers to heart rhythm represented by voltage over time and includes, for example, raw voltage data or a graphical image. The examples given herein do not suggest that they are the only examples or are limited to these examples. Any equivalence may constitute an alternative or addition.

ECG source refers to a device that captures the electrical activity of the heart by means of electrodes, e.g. KardiaMobile 6L ECG device (AliveCor). ECG segments or intervals refer to standard components of the electrical waveform for each heartbeat (e.g. PR, QT), representing individual depolarization and repolarization events of cardiomyocytes. ECG channel electrode(s) of interest refer to the specific leads considered most accurate for QTc measurement in clinical practice (e.g. leads II, III, and V5 on a 12-lead ECG, lead II on a mobile 6-lead ECG).

Baseline models refer to the simple functions upon which one or more MI, algorithms are trained to learn and predict the relationship between input (feature) data and the target variable or label. Examples of ML algorithms include logistic regression, linear regression if predicting a continuous variable like QTc (more suited for image or signal processing), and pre-trained convolutional neural networks for vision-related tasks such as interpretation of ECG quality and baseline rhythm/rate. These ML algorithms may include one or more ML techniques. Examples of ML model/technique(s), structure(s) or algorithm(s) include or be based on, by way of example only but is not limited to, one or more of any ML techniques or algorithm/method that may be used to generate a trained model based on a labeled and/or unlabelled training datasets; one or more supervised ML techniques; semi-supervised ML techniques; unsupervised MI techniques; linear and/or non-linear ML techniques; ML techniques associated with classification; ML techniques associated with regression and the like and/or combinations thereof. Other examples of ML techniques/model structures may include or be based on, by way of example only but are not limited to, one or more of active learning, multitask learning, transfer learning, neural message parsing, one-shot learning, dimensionality reduction, decision tree learning, association rule learning, similarity learning, data mining algorithms/methods, artificial neural networks (NNs), autoencoder/decoder structures, deep NNs, deep learning, deep learning ANNs, inductive logic programming, support vector machines (SVMs), sparse dictionary learning, clustering, Bayesian networks, types of reinforcement learning, representation learning, similarity and metric learning, sparse dictionary learning, genetic algorithms, rule-based ML, learning classifier systems, and/or one or more combinations thereof and the like. The baseline model may also be a function, not strictly requiring the use of ML techniques as described above, such as a formulation: Y=f(Xi, B)+Ei.

More specifically, one or more ML models/techniques may incorporate Wavelet Decomposition, the Kalidas algorithm, the Pan Tompkins algorithm, and an ensemble of ML models including TabNet and XGBoost for detection of the end of the T-Wave to automate the calculation of the QTc interval.

Annotated segments refer to the output of an image or signal annotation technique that is used to detect, classify, and localize segments of the object for computer vision, e.g. an ECG with a labeled T-wave. The annotated segments were used for training the baseline model.

Interpreted heart rhythm/rate refers to the heart rhythm and ventricular rate (e.g. beats per minute, BPM). The interpreted heart rhythm/rate may be determined by ML methods herein described or any other equivalent method for deriving rhythm and rate.

An image or signal processing model refers to the specialized code block that performs analysis and manipulation of a digitized ECG or ECG image (e.g. an ML model). Each code block is designed to optimize QTc precision for the given type of digitized ECG or ECG image (e.g. ECG capturing slow and regular HR or ECG capturing irregular rhythm at fast HR). The image or signal processing model may use one or more ML models/techniques herein described to achieve further optimization or improvement in terms of accuracy. The use of ML model/techniques may not be required if initial accuracy is maintained without such techniques.

QTc measurement refers to the heart-rate corrected QT, the mathematical measurement between two fixed points on an ECG: start of QRS complex, and end of T-wave. The QT is corrected to QTc by way of standard formulae used in clinical practice (e.g. Bazett, Fridericia).

Extraneous data refers to data in ECG or ECG image that is not utilized directly for rhythm interpretation or lead identification by OCR (e.g. noise, artifact), and is thus filtered or masked by the software (e.g. background gridlines).

Fast Fourier Transform (FFT) refers to a measurement algorithm that reduces the number of computations required for N points from $2N^2$ to $2N\lg_2(N)$, e.g. the Cooley-Tukey FFT algorithm. Algorithms include decimation in time or frequency. E.g. the Cooley-Tukey FFT algorithm rearranges input elements in bit-reversed order and subsequently builds the output transform (decimation in time), by recursively breaking up a transform of length N into two transforms of N/2 length (a "divide-and-conquer" algorithm) at each step.

Discrete wavelet transform refers to a technique to transform image pixels into wavelets prior to compression and further coding. The transform is defined by the following equation:

$$W\varphi(j_0, k) = 1/\sqrt{M}\sum f(x)\,\varphi_{j0,k}(x).$$

Clinical data refers to the set of patient characteristics, including demographic information (e.g. age, sex, ethnicity) as well as medical diagnoses (e.g. underlying heart rhythm disorders, presence of implantable pacemaker or cardioverter defibrillator).

ECG databases refer to the compilation of ECGs from a set of patients for use in training or validation of software, e.g. the ANSI/AAMI EC13 Test Waveforms database.

ECG quality for interpretation refers to the signal quality and general readability of an ECG, including but not limited to, e.g. noise and baseline artifact.

Baseline heart rhythm/rate interpretation refers to the ECG rhythm category (e.g. normal sinus rhythm or atrial fibrillation), and HR (BPM) defined by the interval between QRS complexes (heartbeats).

ECG characteristics (e.g. QRS, QT, and T-wave) refer to discrete, standard components of an ECG waveform from each heartbeat produced from cardiomyocyte electrophysiology. The QRS complex represents ventricular depolarization, the T-wave represents ventricular repolarization, and the QT segment represents the period from the start of ventricular contraction to the end of ventricular relaxation. At extremes of length, this segment is associated with an increased risk of developing abnormal heart rhythms (e.g. TdP) or sudden cardiac death.

ECG category refers to the broad ECG class based on heart rate (HR) heart rhythm (e.g. fast and irregular, fast and regular, slow and irregular, slow and regular).

Generated dose recommendation refers to the algorithm-provided dose guidance, based on analysis of ECG features and patient characteristics, which may be submitted for clinician approval (e.g. DoseMeRx, THRC Solutions).

Arrhythmia information refers to the collective descriptions of ECG features, e.g. baseline rhythm, HR, pauses, ectopic beats, and other data that may be collected from cardiac monitoring devices. This information is directly used to guide drug dosing and adjustment. One-shot architecture search refers to an ML training approach whereby only one supernetwork is trained to approximate the performance of every architecture in the search by assigning weights, thereby reducing the computational cost (e.g. combining ML models of different node sizes during model training followed by independent evaluation of performance). Generative adversarial network refers to an approach to generative modeling, an unsupervised learning process in ML that involves automatically discovering and learning patterns within input data using deep learning (e.g. two neural networks repeatedly competing in a game of chess in order to improve the underlying neural networks).

The patient may be fitted with the safety device (e.g. WCD), and an ECG from the portable ECG tool may be compared to the patient's 12-lead ECG to ensure comparable results. The patient will use the mobile ECG device to collect an ECG twice daily (as in the hospital), and the novel software described will analyze each ECG. The software will track QTc over serial ECGs to provide dose guidance (continue medication, reduce dose, or stop). After each dose, a clinician will approve the output ECG and software provided preliminary QTc and dose guidance. The clinician will use this information to determine the best course of action. Specific examples of implementing the invention are provided in the following sections.

Further, the present invention comprises optional steps of ML analysis as well as specialized image-processing code designed to optimize millisecond precision for each ECG category (e.g. irregular versus normal rhythm, fast versus slow rate), maximizing the capabilities of different software tools. This invention is implemented as software code or program. The implementation enhances QTc precision beyond the capabilities of purely image-based or purely artificial intelligence (AI)-based approaches in existence, all of which are universally trained on normal sinus rhythm ECGs at normal HR. Moreover, this software is the first to link QTc interpretation to preliminary drug dose recommendation(s). ML analysis of clinical patient features may be applied selectively. An example of software implementation includes the following combination of steps and substeps. The order of the steps and substeps is exemplary only. That is, the steps and substeps may be carried out in any suitable order or simultaneously where appropriate. Additional steps and substeps may be added or substituted in, or individual steps may be deleted from any of the methods without departing from the scope of the subject matter described herein.

In relation to FIGS. 2 and 3, an example of implementation comprising computational steps 1 to 12 and substeps are described below. The present invention is not however limited to only these steps and substeps, and further steps or substeps may be incorporated into this example, for example, further steps or substeps may be described elsewhere in this application. Similarly, one or more following steps or substeps may be removed without affecting the overall performance of the software and further annotated.

In step 1. Electrocardiogram input is received (e.g. raw signal data or scanned ECG image or a screenshot image of ECG obtained from the mobile device). If applicable, as an option, the image is converted into machine-readable data. Step 2. Data resolution is detected to calibrate the input data (e.g. 10 millimeters per 1 millivolt), and relevant ECG segments are identified (e.g. by optical character recognition) and isolated. Step 3. ECG image segments are digitized into graphical voltage waveforms of black versus white pixels over time, and masking removes extraneous data (e.g. gridlines, artifact). Step 4. Post-processing ensures accurate digitization, filters the noise, and restores any waveform pixels removed by grid masking to generate a continuous waveform for subsequent analysis. Step 5. Horizontal baseline of the ECG may be identified. Individual heartbeats may be marked using wavelet transformation to detect each QRS component. Step 6. As an option, the deep neural network may be trained on large ECG databases to analyze features such as baseline morphology and beat variance. The network may determine 1) whether the ECG may be interpreted based on resolution and signal quality, and 2) baseline heart rhythm/rate. An example of a substep is described below: Substep 6.1. Both Fast Fourier transform and discrete wavelet transform are used to extract features from the frequency/time domain and remove additional noise. This may be deployed without the deep neural network. 6.2. Extracted features for selected channels (extracted ECG segments based on electrodes of interest) are fed into series Transformer-encoder layers. This may be deployed without the deep neural network. 6.3. Embeddings generated by the previous blocks are fed into a series of fully connected layers and then to a softmax function. This may be deployed without the deep neural network. 6.4. As an option, one-shot or few-shot Neural Architecture Search is applied to estimate the performance of each architecture in the search space and find the optimal structure of the transformer network. 6.5. As an option, Generative Adversarial Networks (GANS) are used to generate synthetic data to stress test data acquisition and interpretation by generating synthetic "paper reports" with common artifacts/noise typical of digitized content. 6.6. Model performance is continually evaluated using standard metrics (precision/recall and area under the curve) and qualitatively using interpretable machine learning methods (e.g. Grad-CAM). Step 7. Based on interpreted rhythm and rate, ECG is routed to a specific image processing code (e.g. code block for HR>100 BPM in an irregular rhythm) designed to optimize precision for the given ECG category. Step 8. In each specialized image processing code block, standardized steps may be implemented to label standard heart rhythm waveform points. Step 9 comprises: Substep 9.1. For ECGs interpreted as atrial arrhythmias, waves may be smoothed below an amplitude threshold defined by beat morphology. Substep 9.2. The QRS wave may be identified. 9.2.1. For each heartbeat, the start of QRS is identified by the earliest local maximum of the absolute value of the second derivative (biggest positive or negative change in voltage from horizontal baseline). Substep 9.3. T-wave may be identified. 9.3.1. Latest local maximum is identified for each heartbeat. The end of QT is identified by the intersection between the horizontal baseline and a tangent line drawn automatically through the T-wave inflection point (second derivative=0). Substep 9.4. QT may be computed as the difference between QT_end and the start of QRS. QT may be measured over three successive beats. QT will then be converted to QTc based on standard correction formulae (e.g. $QTcF=QT/RR^{1/3}$) correction, preferred for drug risk assessment). Step 10. Machine learning will support QTc measurement, heart rhythm analysis, and preliminary dose recommendation(s) based on the clinical characteristics of the patient. Substep 10.1. As an option. the deep neural network may be trained on data from prior drug initiation hospitalizations, including dosing patterns in relation to clinical features such as age, sex, medical comorbidities, history of QTc prolongation, presence of internal pacemaker or defibrillator. 10.2. At higher risk QTc ranges (e.g. QTc 490-500 ms), there will likely be a lower threshold to recommend dose reduction if the patient meets specific criteria (e.g. patient is >70 years and female). There may be a higher threshold to recommend dose reduction for a patient who is male, <60 years, and with an internal defibrillator. Step 11. Final rule-based verification will ensure that drug dose modification is recommended if QTc is above high-risk thresholds tested for the given drug (e.g. if QTc≥500 ms, or if QTc is 15% increased from baseline QTc for most antiarrhythmic medications). Step 12. Software output will include preliminary QTc and dosing recommendations for the given patient. This data may be transmitted to the prescribing clinic, wherein the physician will approve each dose. The clinical team will communicate instructions to the patient throughout the heart rhythm monitoring period. This process is further described elsewhere in this application.

Experimental data demonstrating improvement of QTc automation over alternate implementations are shown in Table 1. Software implementation described herein, even absent any machine learning training on clinical data, is superior to the results of existing algorithms, particularly in sensitivity to detect QTc above certain clinically relevant thresholds (e.g. QTc>500 ms, the near-universal threshold for discontinuation of any QTc-prolonging drug).

hospital beds and inpatient resources; and 4. Increased safety since home monitoring may be extended beyond three days inexpensively.

Moreover, the specific implementation of automated electrogram (ECG) analysis with dose guidance provides the following advantages over existing approaches: 1. The first technology to surpass ECG diagnostics and directly guide AF treatment. 2. The first technology to automate ECG interval from a range of input formats, from signal data to ECG images without preprocessing or digitization. 3. The first technology to combine machine learning and image and/or signal processing approaches to maximize QT measurement precision beyond any existing algorithms. 4. The first technology to provide medication dose guidance based on ECG interpretation and clinical data to maximize safety based on patient characteristics (e.g. age, sex, presence of implanted pacemaker/defibrillator device). 5. First technology trained to measure ECG intervals (e.g. QTc) specifically during irregular heart rhythms.

A software prototype has been built, which automates the QTc interval with accuracy 5.2±7.2 milliseconds, surpassing the ECG standard (20 ms), including on patients with highly irregular heart rhythms or fast HR (categories typically challenging and excluded from published testing of existing heart rhythm algorithms). Input data may be an ECG image without preprocessing or digitization. The input data may also be digital or raw signal ECGs as an alternative or via an existing algorithm designed to process ECG signal data.

The input data to the present system may also include data obtained from one or more MCT devices or from WCD devices. The data is included as additional inputs for the machine learning-based dose recommendation algorithm described herein. For example, the MCT device may provide valuable input because the presence of a significant number

TABLE 1

Results of novel QTc automation software on open source hand-annotated ECGs. Input data included ECGs from patients in both normal rhythm and atrial fibrillation (irregularly irregular), including fast atrial fibrillation (the most challenging category for QTc measurement). Results from the hybrid image-processing and machine learning code step(s) in the present application offer 90-91% sensitivity across all QTc thresholds.

| | SafeBeat Rx ML vs Cardiologist-annotated Database (12-lead ECGs) | | |
|---|---|---|---|
| Mean (95% confidence interval) | QTcF ≥ 460 (153/1239) | QTcF ≥ 470 (113/1239) | QTcF ≥ 500 (45/1239) |
| AUC | 0.994 (0.991-0.997) | 0.995 (0.993-0.998) | 0.997 (0.995-1.00) |
| Sensitivity, % | 89.5 (84.7-94.4) | 92.0 (80.7-97.0) | 91.1 (82.8-99.4) |
| Specificity, % | 97.7 (96.8-98.6) | 98.0 (97.2-98.9) | 99.5 (99.1-99.9) |
| PPV, % | 84.6 (79.0-90.1) | 82.5 (75.9-89.2) | 87.2 (77.7-96.8) |
| NPV, % | 98.5 (97.8-99.2) | 99.2 (97.8-99.2) | 99.7 (99.3-1.00) |

Mobile ECG devices, MCT, and WCD devices are used independently in the home setting, but no method, system, or device integrates these tools. The invention fills this critical gap by providing a take-home kit that combines approved hardware with this novel software, fully automating the detection of high-risk heart rhythm changes and providing the prescribing physician with specific dose recommendations based on patient characteristics. This system provides the first alternative to hospitalization by shifting antiarrhythmic drug loading safely to the home environment. Specifically, the invention addresses at least the following unmet needs: 1. Improved medication access for patients; 2. Reduction of healthcare costs; 3. Preservation of of premature ventricular contractions (PVCs), pauses, periods of bradycardia or tachycardia may prompt dose adjustment (typically dose reduction or discontinuation, or in some cases switching to an alternate drug or clinical treatment approach altogether).

It is understood that the MCT hardware uses a small, portable wearable device that provides continuous rhythm monitoring that importantly may be accessed by the physician and medical staff at any time during the monitoring period. As with full-disclosure hospital telemetry systems, MCT provides real-time HR trends as well as arrhythmia alerts. The advantage of MCT is the ability to analyze each heartbeat and prompt emergency responses based on auto-triggers for tachycardia, bradycardia, pauses, PVC, and atrial fibrillation. For the purposes of AAD initiation, PVC detection may be an important feature that, in conjunction with QTc measurement, confers the risk of developing TdP ventricular arrhythmia. Thus in the present system, the arrhythmia information may be incorporated into the interface described herein and presented to the healthcare provider to assist with clinical decision-making. Examples of MCT devices and applications may include but are not limited to: MoMe Kardia (InfoBionic); Core 12, Clip (ACS diagnostics); MCOT, ePatch, MCT 3L (Biotelemetry-Philips); MEMO (Huinno); VitalPatch (VitalConnect); PocketECG (Medilynx); BodyGuardian MiniPlus (Preventice); QardioCore (Qardio); BardyDx CAM, Philips XT, and Heartrak Smart/AF.

FIG. 1 is a block diagram illustrating an example process 100 of the present invention for providing an all-encompassing system for mobile drug initiation. In this example, a patient who is prescribed medication is initially screened for eligibility to receive the take-home SafeBeat Kit'. Initial screening may include baseline lab studies and collection of both a 12-lead ECG and a mobile (e.g. 6-lead) ECG. Once a patient is deemed low risk and is prescribed the SafeBeat Kit™, the patient may be fitted with a WCD and provided a MCT device ("not shown") and a simple handheld mobile ECG device to take home. (If the WCD vest contains sufficient electrodes to measure QTc, the separate mobile ECG device may be obviated. Currently, existing WCDs use non-traditional leads that do not support QTc measurement.) Once the patient takes the kit home, the WCD will begin continuous live rhythm monitoring, and the SafeBeat mobile application will link the patient with the clinic staff. The patient will use the mobile ECG device to collect an ECG twice daily (based on current practice in the hospital), and SafeBeat software will analyze each ECG. Via cloud computing, SafeBeat software will apply ML approaches to analyze each ECG and track QTc over serial mobile ECGs to provide dose guidance (continue medication, reduce dose, or stop). After each dose, the clinic staff will review the ECG, including preliminary QTc and dose guidance. The physician will use this information to determine the best course of action.

In step 101, the patient receives a full 12-lead ECG via a standard ECG machine (101*a*). In step 102, the patient receives a mobile (e.g. 6-lead) electrogram via a handheld device (102*a*). In step 103, the tracings from each machine are compared to ensure the mobile ECG has signal quality and agreement with the standard 12-lead ECG. In step 104, the patient has been deemed eligible for safe antiarrhythmic initiation at home via the SafeBeat Kit'. In step 105, the patient is fitted with a WCD and MCT (105*a*), which are worn throughout the drug monitoring period. Optionally, the WCD may be configured to utilize additional pulse data in order to improve accuracy of the defibrillation and avoid inappropriate shocks. In step 106, the patient obtains a mobile ECG (106*a*) using the portable device. In step 107, the patient's mobile ECG data (107*a*) is transmitted wirelessly to the closest internet receiver (108*a*). In step 108, the mobile ECG data is transmitted from the wireless receiver to the internet. In step 109, analysis is conducted within the cloud-based computing environment. In step 110, machine learning analysis may be applied as an option to the ECG data to interpret heart rhythm and other features further described in FIG. 3. In step 111, further ECG analysis is performed to determine QTc and output a preliminary dose recommendation based on the patient's clinical features and ECG data. In step 112, the information is conveyed via a mobile application to the prescribing clinician (e.g. a physician or other healthcare provider). The physician (113) will use this information to determine the best course of action for the patient (e.g. continue the medication, reduce the dose, or stop the medication). In step 114, the clinical team will communicate the physician-approved dosing to the patient and confirm understanding. This process will repeat once the next mobile ECG is taken for the duration of the chosen monitoring period.

Figure 4:
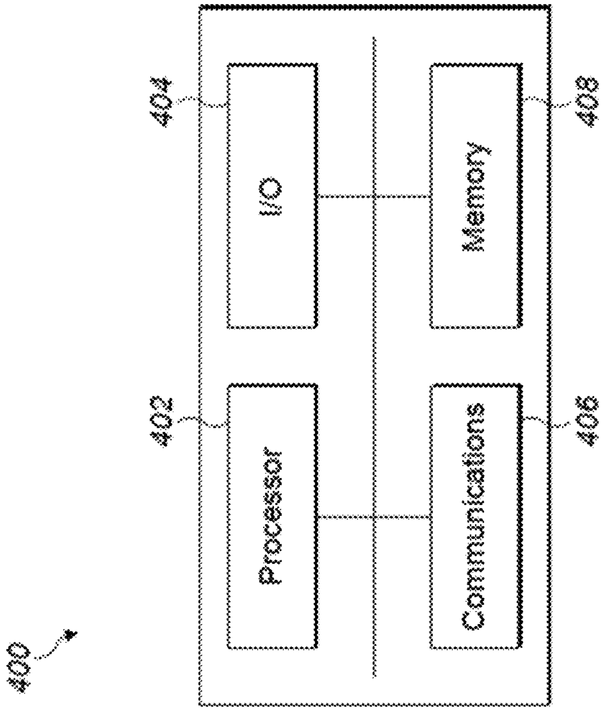
FIG. 4 is a block diagram illustrating an example of a computing device suitable for implementing an aspect of the invention.

Steps 101 to 114 may be suitable for implementing on hardware embedded with apparatus/system depicted for example in FIG. 4. Optionally, these steps and any step described herein are not limited to software (or firmware) implementation and may also be hard-coded onto the hardware. The hardware for implementation may include but are not limited to one or more hardware logic components such as Field-programmable Gate Arrays, Program-specific integrated circuits, Program-specific Standard Products, System-on-a-chip systems, Complex Programmable Logic Devices or any GPU-based acceleration chip. These hardware logic components are suitable for implementing any of the subsequent steps or software code.

Figure 2:
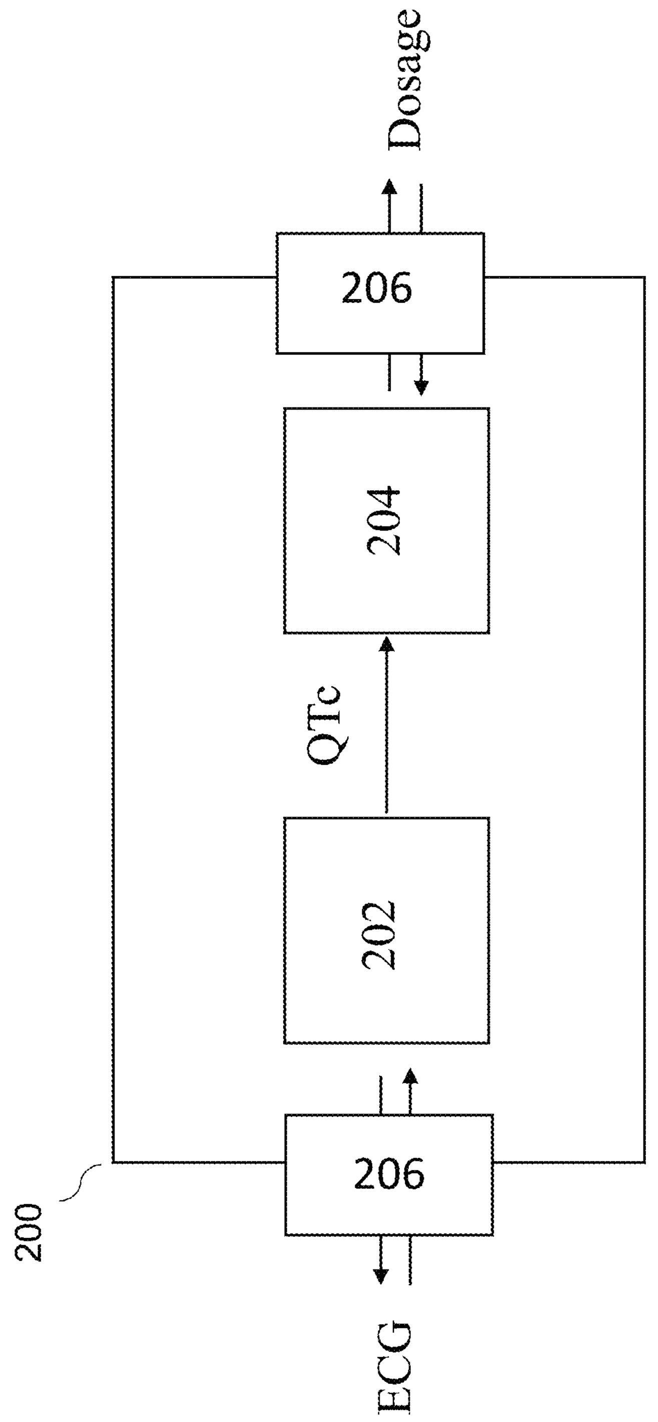
FIG. 2 is a schematic diagram illustrating an example system for secured transmission of a QTc measurement for dosage guidance and monitoring according to aspects of the invention.
Figure 3A:
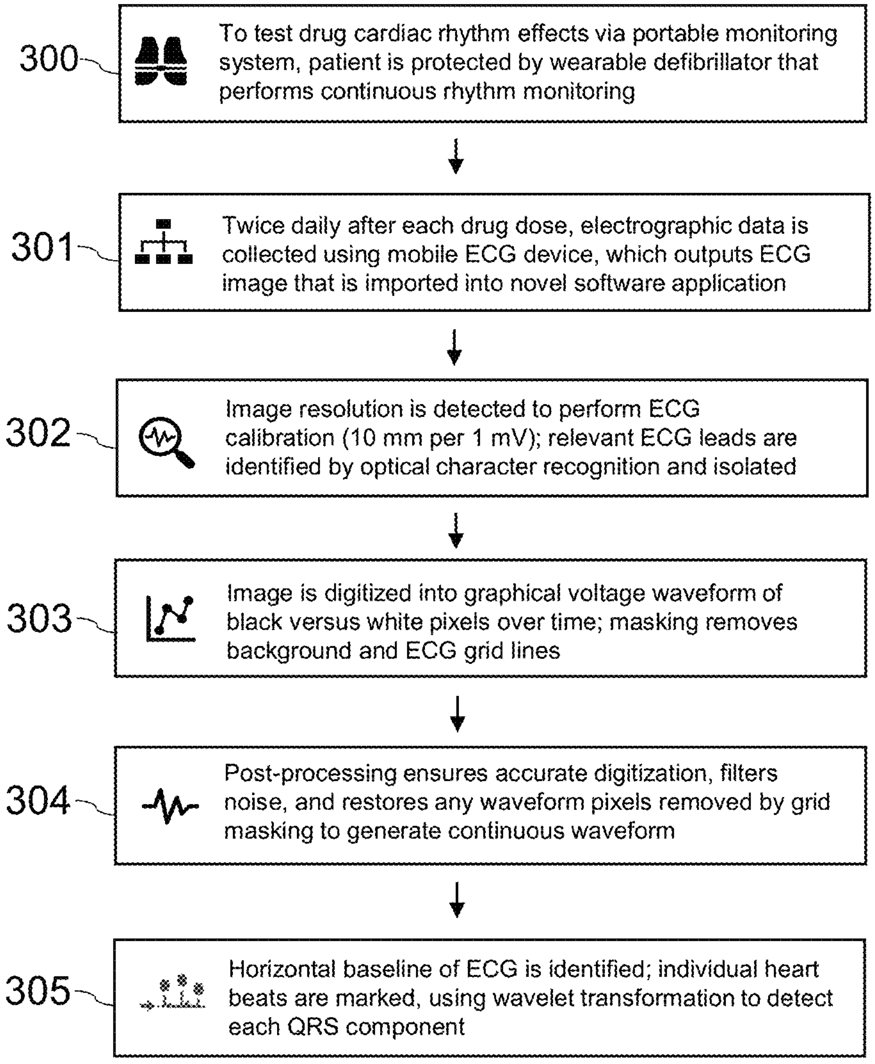
FIG. 3 is a flow diagram illustrating an example of computing a corrected QT interval measurement based on ECG data according to an aspect of the invention.
Figure 3B:
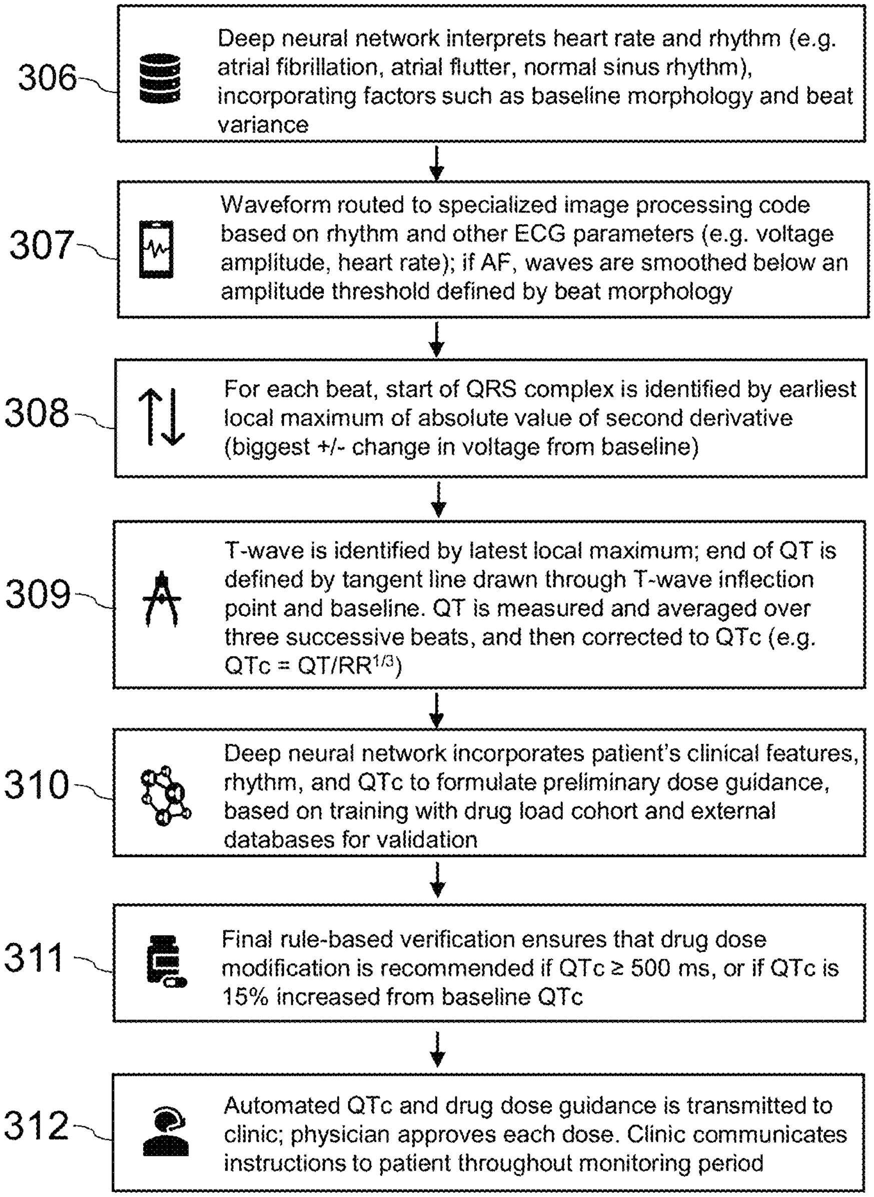

FIG. 2 is a schematic diagram illustrating an example system including steps for secured transmission of a QTc measurement for dosage guidance and monitoring. The system 200 provides interactive remote drug dose guidance and physiologic response monitoring for a patient. The system comprises a first module 202 configured to interface 206 with the patient using a secured communication, wherein the first module 202 is adapted to receive periodically, through the secured communication, ECG data from the patient for a predetermined time period until completion of a drug load. The first module 202 may include an interface 206 that receives from the patient, through the secured communication, one or more inputs in relation to the dosing of a drug. These inputs may be instructions to modify the dosage of AAD such as flecainide, amiodarone, dronedarone based on patient QTc. The inputs may also include personal information of the patient (e.g. clinical characteristics), and a selection of drugs for dosing or a stage of dosing for a dosed drug. This is important because factors like kidney function and body weight commonly affect the dosing recommendations. The interface 206 may display said one or more inputs or store said one or more input for display at a later time to the patient. The interface 206 may also display a graphical representation of the QTc. The QT segment is visually demarcated. The QTc may be annotated with automated measurements, i.e. the annotation may be toggled on or off by the user. This may be done manually or in an automated manner. The interface 206 is further illustrated according to FIG. 5 and FIG. 6.

The system further includes a second module 204 configured to generate one or more QTc measurements based on the periodically received ECG data and provide said one or more dosage recommendations in a sequential manner, within the predetermined time period, with each dosage recommendation provided based on said one or more QTc measurements. The second module 204 may be configured to cleanse the received ECG data; extract ECG segments from cleansed electrocardiographic data based on ECG channel electrode(s) of interest; provide one or more baseline models trained with annotated segments to generate interpreted heart rhythm/rate based on the extracted ECG segments; select an image or signal processing model based on the interpreted heart rhythm/rate, and apply the selected image or signal processing model to the cleansed electrocardiographic data to generate the QTc measurement. One or more dosage recommendations may be generated based on the QTc measurements to be displayed on interface 206.

In addition, the system may be used for clinical decision-making via a MCT device. The system may have one or more modules configured to interface with a patient via a secured communication. One or more modules are adapted to receive periodically, through the secured communication, ECG data from the patient for a predetermined time period until the clinical decision is made, and wherein said one or more modules are further configured to exhibit arrhythmia information to an interface based on input from the MCT device, wherein the MCT device is adapted to provide the arrhythmia information in accordance with the clinical decision. The system may include a separate module configured to generate one or moreQTc measurements based on the periodically received ECG data and and arrhythmia information to provide clinical decision-making based on said one or more QTc measurements within the predetermined time period.

In one example, any system described herein may be used for providing dosage recommendations by referencing the QTc measurements and one or more clinical metrics. The first module 202 of the system or the system itself may be configured to perform safety checks based on the cardiac physiology of the patient prior to dosing. The first module 202 may also transmit patient-related input to and from a third-party application using secured communication, wherein the patient-related input is displayed to the patient. In another example, the first module 202 of the system or the system itself may be configured to transmit ECG data to and from a third-party application using the secured communication for determining the QTc measurements. In yet another example, the first module 202 of the system or the system itself may be configured to receive and transmit information to and from a third-party through the secured communication, wherein said information relates to said one or more dosage recommendations, a drug, and/or psychological condition of a patient or physical condition of a patient. In yet another example, the second module 204 of the system or the system itself may be configured to receive and process one or more user inputs, wherein said one or more user inputs are used for providing said one or more dosage recommendations in accordance with the QTc measurements.

With respect to the second module 204, for example, a QTc measurement may be derived using electrocardiographic data using the system. The system may start from ECG data that are processed or cleansed. The ECG segments are extracted from the ECG data based on the ECG channel electrode(s) of interest. The extracted segments are processed. Based on the extracted segments, baseline models are trained and used to generate interpreted heart rhythm/rate. An image processing or signal processing model is selected based on the generated interpreted heart rhythm/rate. The selected image or signal processing model is applied to cleansed ECG data for outputting an accurate QTc measurement. Fast Fourier transform and a discrete wavelet transform may be applied to the electrocardiographic data. Other numerical analysis and functional analysis techniques yielding the same or similar results may be applied in addition to or in place of either the Fast Fourier transform or the discrete wavelet transform.

Optionally, the QTc measurement may be provided to one or more machine learning models for generating a dose recommendation for a patient. The generated dose recommendation is outputted to a user via an interface 206 described here. The interface 206 may be presented using a device such as a smartphone. Interface 206 establishes secure communication between the patient and the physician. The communication progresses dosage recommendation for delivery of one or more types of medication based on physiological parameters of the patient communicated through the interface 206. The dose recommendation may be validated based on a risk threshold associated with QTc for a given drug. As another option, a dosing recommendation is generated based on said QTc measurement, wherein the computed QTc is derived from QT.

The research approach designed to validate the software in this invention also remains distinct from recent studies by 1) providing a rigorous gold standard from multiple cardiologists and electrophysiologist QT readers fully blinded to clinical data (and with no financial conflict, unlike Giudicessi, John R., et al., 2021); 2) specifically training the algorithm in this invention on an AF drug load cohort (unlike the normal rhythm datasets used in published algorithms), using both clinical data and serial ECGs; and 3) testing the algorithm on additional open-source ECG databases to prove external validity. These features will continue to make the described invention a unique clinical tool designed to redefine the standard of care by meeting high safety standards for commercialization.

In another example, in computing the QTc measurement, the system (1) receives electrocardiogram at least one ECG source; optionally, a Fast Fourier transform, and a discrete wavelet transform may be allowed to the electrocardiographic data. The system (2) cleanses the electrocardiographic data; optionally, the electrocardiographic data is filtered to remove residual noise and artifacts based on one or more predetermined baseline. The image resolution within the electrocardiographic data is detected provided that the filtering is successful. Once detected, the ECG data may be converted to machine-readable format (as an option only) based on the detected image resolution. The raw ECG signal may also be used. The system extracts ECG segments from cleansed electrocardiographic data based on ECG channel electrode(s) of interest. The system (3) provides one or more baseline models trained with annotated segments to generate interpreted heart rhythm/rate based on the extracted ECG segments. As an option, one or more baseline models may be trained using clinical data and ECG databases to recognize when ECGs are of sufficient quality for interpretation, and to learn baseline heart rhythm/rate interpretation. As another option, one or more baseline models may be optimized using a one-shot architecture search. A generative adversarial network may also be applied to generate synthetic data with artifacts for optimizing said one or more baseline models. The system (4) selects an image or signal processing model based on the interpreted heart rhythm/rate; the image or signal processing model may be configured to identify one or more ECG characteristics. One or more ECG characteristics may comprise horizontal baseline, QRS, QT, and T-wave. The system (5) applies the selected image or signal processing model to the cleansed electrocardiographic data, wherein the image or signal processing model outputs the QTc measurement. The image or signal processing model may comprise image processing code block(s) optimized for a given ECG category. The outputted QTc may be used to guide drug dosing. For example, QTc rising ≥500 ms, or QTc increasing 15% from baseline QTc for most antiarrhythmic medications will warrant reduction or discontinuation of the medicine. The output dose may be subject to both automated QTc measurement and these final dose rules, in order to provide clinically accurate recommendations. The drug dose guidance itself may be accomplished remotely via analysis from a wearable ECG device. Alternatively, and additionally, the QTc measurement may be used with or applied on a wearable defibrillator or defibrillator device to the extent that the defibrillator device may be configured to use additional pulse sensor data. The QTc automation in this invention effectively guides remote AAD initiation with a precision superior to any existing methods.

In yet another example of the corresponding steps above, the electrocardiographic input is initially converted into machine-readable data. From the input data, image resolution is detected to calibrate the input data, and relevant ECG segments may be identified and isolated in a suitable format. ECG image segments may be digitized into graphical voltage waveforms of black versus white pixels over time, and masking removes any extraneous data such as gridlines or artifacts. In effect, this ensures accurate digitization, filters the noise, and restores any waveform pixels removed by grid masking to generate a continuous waveform for subsequent analysis.

Further, the horizontal baseline of the ECG may be identified. Individual heartbeats may be marked using wavelet transformation to detect each QRS component. A deep neural network trained on large ECG databases may be used to analyze features such as baseline morphology and beat variance. Other machine learning models or techniques may also be employed in addition or in place of the deep neural network. The network or model will determine 1) whether the ECG may be interpreted based on resolution and signal quality, and 2) baseline heart rhythm/rate.

More specifically, both Fast Fourier transform and discrete wavelet transform may be used to extract features from the frequency/time domain and remove additional noise. Both techniques may be replaced with a similarly equivalent combination of one or more numerical analysis and/or functional analysis techniques. The extracted features for selected channels (extracted ECG segments based on electrodes of interest) may be fed into series Transformer-encoder layers or such similar layers of a network model. Embeddings generated by the previous blocks may be fed into a series of fully connected layers and then to a SoftMax type function or alternative loss functions. One-shot or few-shot Neural Architecture Search may be applied to estimate the performance of each architecture in the search space and find the optimal structure of the transformer network. In addition, generative Adversarial Networks (GANS) may be used to generate synthetic data to stress test data acquisition and interpretation by generating synthetic "paper reports" with common artifacts/noise typical of digitized content. Model performance is continually evaluated using standard metrics (precision/recall and area under the curve) and qualitatively using interpretable ML methods (e.g. Grad-CAM). Alternative ML methods may be included as part of this process to improve the results.

Based on interpreted rhythm and rate, ECG is routed to a specific image or signal processing code (e.g. code block for HR >100 BPM in an irregular rhythm) designed to optimize precision for the given ECG category. The image or signal processing code may apply one or more ML techniques or an alternative algorithm for the selection or routing process. The image or signal processing model may be configured based on interpreted heart rhythm/rate to identify one or more ECG characteristics for which the output measurement may be based.

More specifically, in each specialized image or signal processing code block, standardized steps may be implemented to label standard heart rhythm waveform points. For ECGs interpreted as atrial arrhythmias, waves may be smoothed below an amplitude threshold defined by beat morphology. QRS wave may be identified. For each heartbeat, the start of QRS is identified by the earliest local maximum of the absolute value of the second derivative (biggest positive or negative change in voltage from horizontal baseline). T-wave may be identified. The latest local maximum is identified for each heartbeat. The end of QT is identified by the intersection between the horizontal baseline and a tangent line drawn automatically through the T-wave inflection point (second derivative=0). QT may be computed as the difference of QT_end and the start of QRS. QT may be measured and averaged over three successive beats. QT will then be converted to QTc based on standard correction formulae (e.g. $QTcF=QT/RR^{1/3}$ correction, preferred for drug risk assessment).

Further, ML analysis will incorporate QTc measurement, heart rhythm, and clinical characteristics of patients to provide preliminary dose recommendation(s). For example, a deep neural network may be trained on data from prior drug initiation hospitalizations, including dosing patterns in relation to clinical features such as age, sex, medical comorbidities, history of QTc prolongation, presence of internal pacemaker or defibrillator. At higher risk QTc ranges (e.g. QTc 490-500 ms), there will likely be a lower threshold to recommend dose reduction if the patient meets specific criteria (e.g. patient is >70 years and female). The rule-based or other similar verification will ensure that drug dose modification is recommended if QTc is above high-risk thresholds tested for the given drug (e.g. if QTc ≥500 ms, or if QTc is 15% increased from baseline QTc for most antiarrhythmic medications).

The output of the software may include preliminary QTc and dosing recommendations for the given patient. This data may be transmitted to the prescribing clinic, wherein the physician will approve each dose. The clinical team will communicate instructions to the patient throughout the heart rhythm monitoring period.

Additionally and alternatively, further ML analysis or one or more ML models may be deployed for the section and processing of ECG data. Specifically, 1) selection of the ideal ECG lead for subsequent analysis, and 2) selection of preferred heartbeat(s) presented for approval from all beats in the available heart rhythm data. The section may be performed by a selection module. The selection module may be incorporated into the first or second module or any other module of the system. The ML analysis takes place when or beyond rhythm pre-classification and dose recommendation, detailed as 1) and 2).

FIG. 3 includes 3A and 3B. FIG. 3 details an example software for a patient undergoing mobile drug monitoring using the QTc measurement generated. Any aspect of this example may be combined as appropriate with any other aspect(s) of the invention. The software combined with portions of the SafeBeat Kit™ (e.g. mobile ECG device only) may be used to support chronic care management and remote monitoring through ECG based data (e.g. arrhythmias, heart rate) as well as remote therapeutic monitoring (e.g. medication dosing and compliance) for long term monitoring (e.g. periods ranging from a month to years) which may be reimbursable by insurance companies. Patients may input their compliance with prescribed medications (e.g. through twice daily attestation of taking recommended dosage). This information will populate into the SafeBeat portal, and the patient's healthcare provider's clinic may be notified, who will review the information monthly and provide any clinical recommendations as needed.

In step 300 (FIG. 3A), a patient is protected by the WCD throughout the monitoring period for e.g. AAD initiation. This defibrillator may be performing continuous rhythm monitoring, in order to deliver defibrillation if needed to treat an adverse dysrhythmia. In step 301, the patient collects electrographic data via a mobile heart rhythm device. This may be conducted twice per day, 2 hours after each medication dose, to replicate current practice for AAD initiation in the hospital. In step 302, as an optional step, the image of the ECG data is analyzed to detect image resolution for ECG calibration (e.g. 10 mm per 1 mV). The relevant ECG segments may be identified (e.g. by optical character recognition) and extracted for analysis. In step 303, as an optional step, the ECG image segments may be digitized into graphical voltage waveform(s) of black versus white pixels over time. Masking may remove any extraneous data such as background ECG grid lines or artifacts. In step 304, as an optional step, post-processing ensures accurate digitization, filters the noise, and restores any waveform pixels removed by grid masking to generate a continuous waveform for subsequent analysis. In step 305, the horizontal baseline of the ECG may be identified. Each individual heartbeat may be marked using wavelet transformation to detect each QRS component. In step 306 (FIG. 3B), machine learning analysis (e.g. deep neural network trained on large ECG databases) may be used to analyze features such as baseline morphology and beat variance. This analysis is performed optionally to improve the QTc measurement. This analysis will include 1) whether the ECG may be interpreted based on resolution and signal quality, 2) baseline heart rhythm (e.g. atrial fibrillation, atrial flutter, normal sinus rhythm), and 3) baseline HR. Analysis may include both Fast Fourier transform and discrete wavelet transform to extract features from the frequency/time domain and remove additional noise. Both techniques may be replaced with similarly equivalent combinations of one or more numerical analysis and/or functional analysis techniques. The extracted features for selected channels (extracted ECG segments based on electrodes of interest) may be fed into series Transformer-encoder layers or such similar layers of a network model. Embeddings generated by the previous blocks may be fed into a series of fully connected layers and then to a softmax type function or alternative loss functions. One-shot or few-shot Neural Architecture Search may be applied to estimate the performance of each architecture in the search space and find the optimal structure of the transformer network. In addition, generative Adversarial Networks (GANS) may be used to generate synthetic data to stress test data acquisition and interpretation by generating synthetic "paper reports" with common artifacts/noise typical of digitized content. Model performance is continually evaluated using standard metrics (precision/recall and area under the curve) and qualitatively using interpretable ML methods (e.g. Grad-CAM). Alternative ML methods may be included as part of this process to improve the results. In step 307. based on interpreted rhythm and rate. ECG is routed to a specific image processing code (e.g. code block for HR >100 BPM in an irregular rhythm) designed to optimize precision for the given ECG category. The image processing code may apply one or more ML techniques or an alternative algorithm for the selection or routing process. The image or signal processing model may be configured based on interpreted heart rhythm/rate to identify one or more ECG characteristics for which the output measurement may be based. For ECGs interpreted as atrial arrhythmias, waves may be smoothed below an amplitude threshold defined by beat morphology. In step 308, standardized steps may be implemented in each specialized image processing code block to label standard heart rhythm waveform points. For each heartbeat, the start of the QRS complex is identified by the earliest local maximum of the absolute value of the second derivative (biggest positive or negative change in voltage from horizontal baseline). In step 309, T-wave may be identified by the latest local maximum for each heartbeat. The end of QT may be identified by the intersection between the horizontal baseline and a tangent line drawn automatically through the T-wave inflection point (second derivative=0). QT is computed as the difference between QT_end and the start of QRS. QT may be measured and averaged over three successive beats. QT will then be converted to QTc based on standard correction formulae (e.g. $QTcF=QT/RR^{1/3}$ correction, preferred for drug risk assessment). In step 310, additional ML analysis may incorporate QTc measurement, heart rhythm, and clinical characteristics of the patient to provide preliminary dose recommendation(s). For example, a deep neural network will guide dosing by training on data from prior drug initiation hospitalizations, including dosing patterns in relation to clinical features such as age, sex, medical comorbidities, history of QTc prolongation, presence of internal pacemaker or defibrillator. At higher risk QTc ranges (e.g. QTc 490-500 ms), there may be a lower threshold to recommend dose reduction if the patient meets specific criteria (e.g. patient is >70 years and female). In step 311, rule-based or other similar verification will ensure that drug dose modification is recommended if QTc is above high-risk thresholds tested for the given drug (e.g. if QTc ≥500 ms, or if QTc is 15% increased from baseline QTc for most antiarrhythmic medications). In step 312, the output of the software will include preliminary QTc and dosing recommendation(s) for the given patient. This data may be transmitted to the prescribing clinic, wherein the physician will review the software-provided information and approve each dose. The clinical team will communicate instructions to the patient throughout the heart rhythm monitoring period. The system for interfacing is further described elsewhere in the application.

It can be understood that following the dosage recommendation or rhythm pre-classification, one or more ML models may be used. One or more ML models are configured to select for the preferred heartbeat(s) presented for approval from all beats in the available heart rhythm data or an ideal ECG lead to be subsequently analyzed either manually or automatically. The analysis may be part of a feedback loop or process within the system.

Further, one or more MI, models may also be adapted to detect characteristic discharge patterns that are measured by a detector device. The detector device is configured to identify defibrillation events automatically via one or more ML models or algorithms trained on characteristic discharge patterns in the heart rhythm tracing. The detector device may be part of the present system. The detected characteristic discharge patterns may serve as an alert of a patient's health or prompt action by the clinical team during dosing or monitoring while using the present system. The detector device may be a defibrillator.

For example, the SafeBeat Kit™ may be able to detect events of defibrillation discharges (shocks) delivered by a defibrillator (whether a wearable cardioverter defibrillator, implanted cardioverter defibrillator, or automated external defibrillator) through a recognition algorithm (e.g. machine learning) that detects the characteristic discharge pattern that is measured by any of the other components of the SafeBeat Kit™ (e.g. mobile cardiac telemetry, mobile ECG, or the wearable cardioverter defibrillator). This detection may then be sent as an alert to the patient's healthcare providers and clinic, or configured by the healthcare provider to also send an alert to emergency services, based on the number of defibrillation discharges that occur within a specified time period.

FIG. 4 is a block diagram illustrating an example computing apparatus/system 400 that may be used to implement one or more aspects of the systems, apparatus, methods, and/or processes combinations thereof, modifications thereof, and/or as described with reference to FIGS. 1 to 3 and/or as described herein. Computing apparatus/system 400 includes one or more processor units 401, an input/output unit 402, communications unit 403, where the communications unit may comprise an interface is 206, a memory unit 404 in which the one or more processor units 401 are connected to the input/output unit 402, communications unit/interface 403/206, and the memory unit 404. In some embodiments, the computing apparatus/system 400 may be a server, or one or more servers networked together. In some embodiments, the computing apparatus/system 400 may be a computer or supercomputer/processing facility or hardware/software suitable for processing or performing the one or more aspects of the systems, apparatus, methods, and/or processes combinations thereof, modifications thereof, and/or as described with reference to FIGS. 1 to 5 and/or as described herein. The communications interface 403/206 may connect the computing apparatus/system 400, via a communication network, with one or more services, devices, the server systems, cloud-based platforms, systems for implementing subject-matter databases and/or knowledge graphs for implementing the invention as described herein. The memory unit 404 may store one or more program instructions, code or components such as, by way of example only but not limited to, an operating system and/or code/components associated with the processes/methods as described with reference to FIGS. 1 to 3, additional data, applications, application firmware/software and/or further program instructions, code and/or components associated with implementing the functionality and/or one or more functions or functionality associated with one or more of the methods and/or processes of the device, service and/or servers hosting the processes/methods/systems, apparatus, mechanisms and/or systems/platforms/architectures for implementing the invention as described herein, combinations thereof, modifications thereof, and/or as described with reference to at least one of the FIGS. 1 to 3 and 5.

Figure 5:
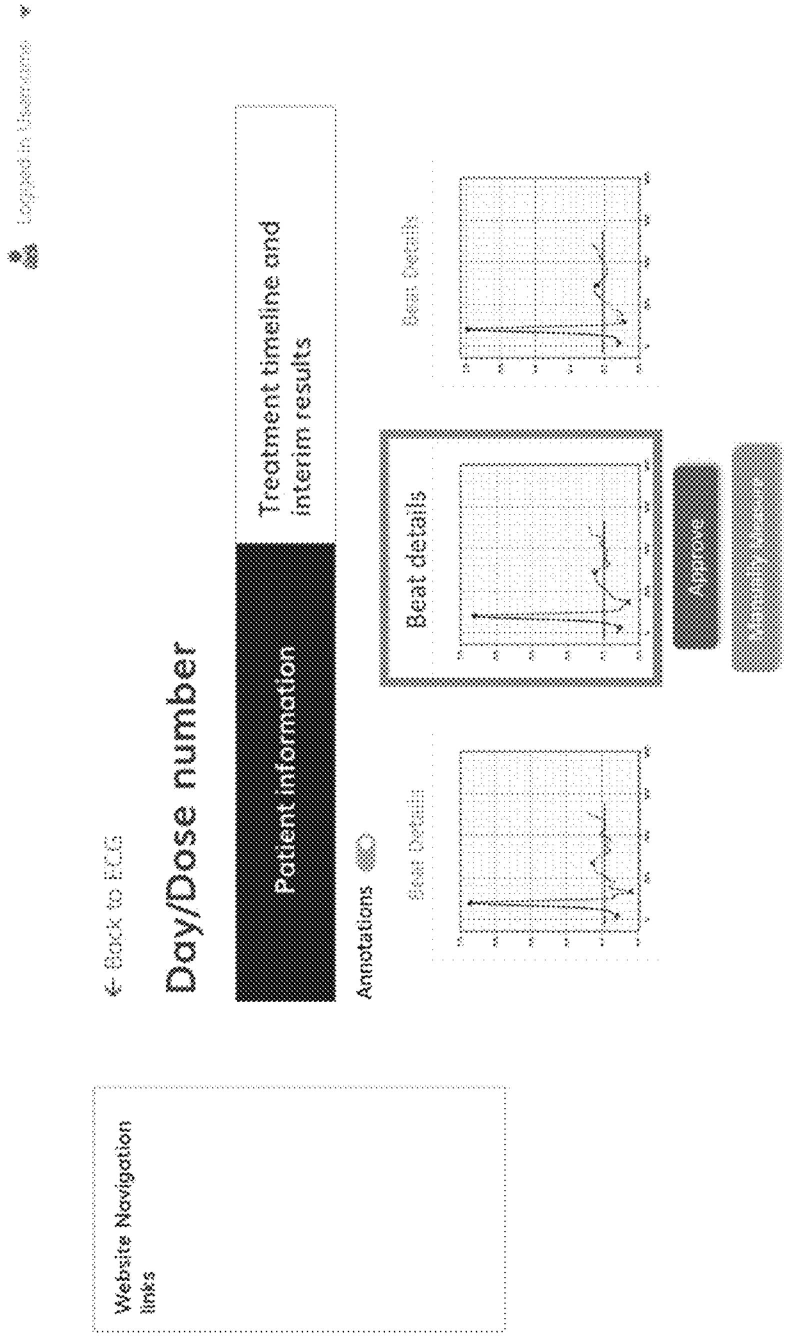
FIG. 5 is a pictorial diagram of the system and interface for transmission of secured a corrected QT interval measurement according to an aspect of the invention.

FIG. 5 is a pictorial diagram of interface corresponding to FIG. 2 interface 206 for transmission of a secured QTc measurement. The interface may be part of one or more modules of the overall system or a separate module external to the system. The interface is configured to display a patient's medical information or other data to the physicians or medical professionals using secured communication. The medical information or other data includes but are not limited to the personal information of the patient, and a selection of drugs for dosing or a stage of dosing for a dosed drug. For example, a predetermined time period until the completion of a drug load, ECG data from the patient may be displayed on the interface. The interface may also receive, through secured communication, one or more inputs in relation to the dosing of a drug. These inputs may be representative of actions or procedures such as approving the ECG received based on the available data or taking additional measurements from the patient as needed. The inputs displayed on the interface may be stored and displayed at a later time. The ECG may be displayed as a representation of the QTc graphically. That is, the QT segment may be visually demarcated and/or annotated with automated measurements, where the visualization of which may be toggled on or off.

In the figure, an exemplary dosing session or treatment lasting multiple days is shown for a patient using the interface. The interface is configured for managing a plurality of patients, including the patient undergoing the treatment. Information associated with the patient is transmitted via a secured communication channel and displayed on the interface. The ECG and the QTc are graphically shown to the physician managing the treatment. The physician is able to provide additional input, optionally based on a selection of inputs, in this case, whether to approve or take an additional manual measurement based on the ECG and the QTc data as well as other information from the interface. In the treatment, the physicians are enabled by the interface to make dosage selections or recommendations based on analysis from the reviewed ECGs. The recommendation process may be assisted by one or more ML models/techniques described herein. The ML models/techniques are configured to predict based on the ECG data and patient profile what is the recommended dosage for the drug. The physicians are able to consider the output shown on the interface and make informed decisions for the patient w.r.t the treatment as the period of treatment progresses.

In one example, the physician interface may display patient details, including multiple patient identifiers; details associated with medication, including but are not limited to name and prior dosages. The interface may also include, for example, a progress bar demonstrating the doses the patient has taken out of the required initiation doses, the default heartbeat selected by software shown alongside alternate preferred heartbeats, and global metrics (clinical metrics) including heart rhythm, HR, and stability of QTc measurement relative to prior measurements. In one example, a graph may be displayed on the interface to provide a visual trend of QTc relative to well-established safety zones, e.g. dangerously high if greater than 500 ms.

The physician and clinical team may be enabled to or granted permission by the system to review prior ECGs with corresponding measurements and medication dosing, in order to provide informed clinical decisions based on the patient's responses to prior dose adjustments. Physicians may have the ability to add notes relating to diagnosis or overall assessment of the ECG through an interactive text box access through an interactive button "Add ECG note," not shown in the figure. Examples of added notes may include but are not limited to diagnosis notes such as notes related to "Normal Sinus Rhythm," "Atrial Flutter," or "Atrial enlargement." The purpose of the interactive button for adding notes is to further simplify or streamline medical documentation or billing needs and requirements. The interactive button may be an optional feature or component of the interface or as part of the system.

In accordance, the physician may be able to proceed with several different options for QTc determination. For example, these options may include: 1) The physician may approve the default heartbeat and corresponding details (e.g. QTc measurement) provided by the SafeBeat Rx software, with a single click; 2) the physician may override the default beat by selecting an alternate beat among multiple software-provided beat options; 3) the physician may choose to measure QTc manually by selecting to view the full rhythm strip or multi-lead ECG recording, and using inbuilt measurement tools that automatically compute QTc from QT and RR interval selections, per standard formulae. In many views, the physician may be able to zoom in for better visualization and more precise manual measurement. Annotations made by the software to demarcate certain intervals on each heartbeat waveform (e.g. beginning of Q, end of T-wave) may be toggled on or off per physician preference. QTc for all beats on the rhythm strip may also be presented to enable a more holistic determination of QTc values for the entire ECG. Also, in the event that there is no interpretable beat in the ECG recording that is suitable for QTc measurement (whether automated or manual) for reasons generally extrinsic, but possibly intrinsic, to the software (e.g. signal noise due to patient movement, or incomplete recording due to patient interruption), physician and/or staff may be presented with an option to notify the patient to repeat the ECG measurement, with additional instructions to the patient likely to improve the ECG signal recording quality. For example, the above may be presented on the interface as an interactive button for "Notify patient to retake ECG and be more still," not shown in the figure.

Following QTc approval, the software-recommended dose may be presented. The physician may again have multiple options for dose determination. 1) The physician may approve the recommended dose with a single click. 2) The physician may choose to override the default dose by selecting an alternate dose among standard dosing options for the given medication per pharmaceutical package labeling. Dosing options may also include an option to discontinue the medication, which the physician may recommend for reasons not captured by software ECG analysis (e.g. patient needs to interrupt the mediation initiation protocol for noncardiac reasons). If concerned, the physician may also be presented with an option to initiate a telephone call to the patient directly at this stage, if there are further instructions to convey beyond dosing instructions. All actions performed by means of the mobile ECG device by the patient or by means of the interface by patient, physician, clinic staff member, or software administrator may be logged with time and date for the purposes of record keeping and displayed to the physician, clinic staff, and/or software administrator as a reviewable history that may be exported as a human-readable file that may be used for purposes such as medical documentation, billing, or legal inquiry. For example, the above actions may be presented on the interface as an interactive text box "Action log," which encompasses one or more interactive buttons for exporting the contents "Export PDF" or "Export Excel." The interactive text box supports secure messaging from physician to staff, from staff to physician, physician to patient, and administrator to physician/staff/patient. The interactive text box may be in the form of a message tab such as to allow for presentation or interaction with said "Action Log." The interactive text box and the buttons are part of the interface but are not shown in the figure.

Further, users of the system, including patients, physicians, clinic staff members, administrators, or any other user, whether remotely or locally using the system, are categorically defined such that each user may retain different security permission. For example, the admin user may be a "Super User" that may override any portion of the system configuration, i.e. manually uploading an ECG, selecting a beat/manually measure, and manually suggesting a dose or providing a recommendation as such.

It is understood that the communications between the users of the system are encrypted. The encryption may be symmetric and/or asymmetric to satisfy data security and personal data standards from a plurality of jurisdictions or countries with respect to the applicable guideline or standards. For example, security features may include Secure Sockets Layer (SSL) encryption, secured logins for all users, automatic time-outs, restricted access, and not including any protected health information (PHI) in unsecured notifications or alerts sent to users. For example, in the US, the communication and storage of any communicated data shall be HIPAA-compliant and compliant according to any state law.

Figure 6:
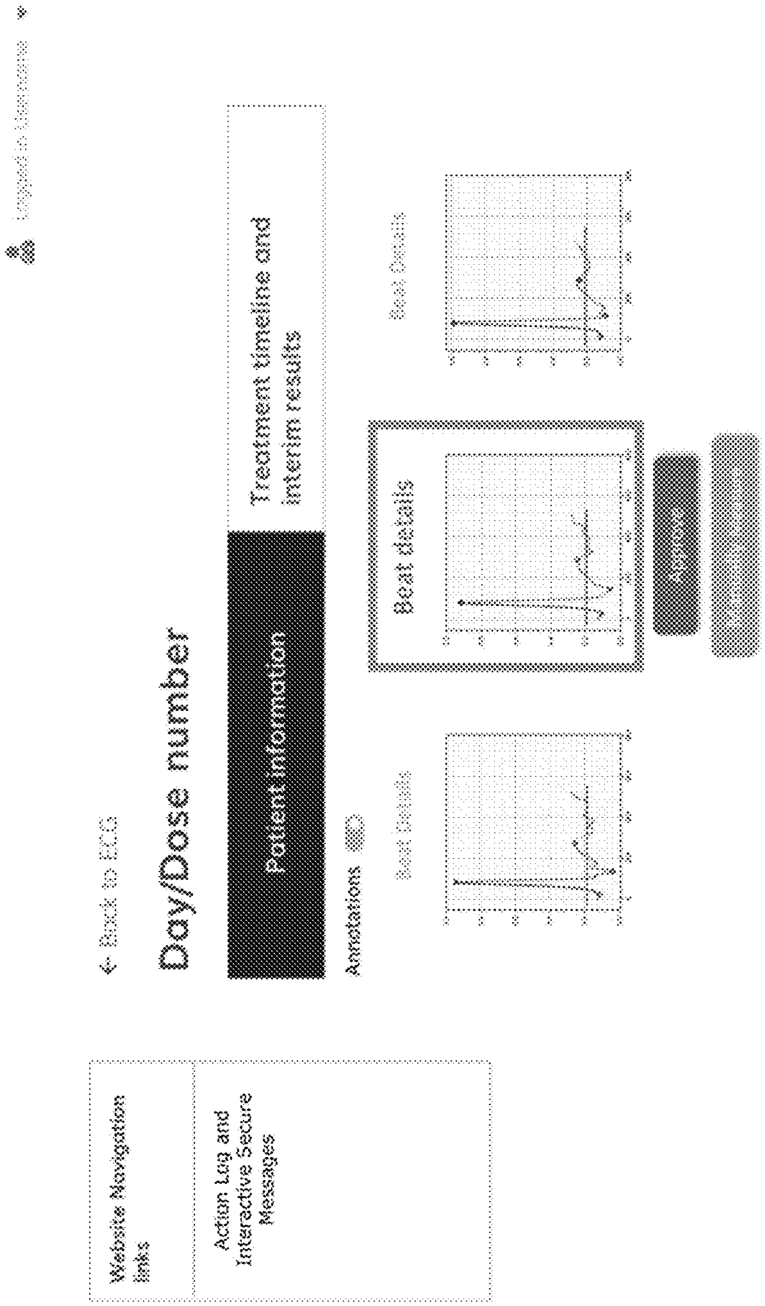
FIG. 6 is a pictorial diagram of the system and interface according to an aspect of the invention.

FIG. 6 is another pictorial diagram of interface 206 of FIG. 2. The interface is configured to transmit a QTc measurement along with other inputs in a secured manner from each class or category of system users when the users are using the system and providing outputs based on the QTc measurement and the associated inputs. The figure shows features or components of the interface, which includes the features or components described in the sections above or described and illustrated in accordance with FIG. 5. Some of the features described are not shown in the figure but are included as part of the interface and the overall system.

It may be understood that the benefits and advantages described above may relate to one embodiment or may relate to several embodiments. The embodiments are not limited to those that solve any or all of the stated problems or those that have any or all of the stated benefits and advantages. Variants should be considered to be included in the scope of the invention. In particular, the various features or components of the interface, including features not shown in the figure, help minimize the number of steps or clicks in an ergonomic manner such that efficiency is increased when a user uses the system or any of the underlying methods for obtaining or submitting a dosage recommendation.

Options described below may be combined with any aspects and/or one or more options of the present disclosure. As an option, cleansing said electrocardiographic data further comprising: filtering said electrocardiographic data to remove residual noise and artifact based on one or more predetermined baseline; detecting image resolution within said electrocardiographic data; converting said electrocardiographic data to machine-readable format based on the detected image resolution. As an option, applying a Fast Fourier transform and a discrete wavelet transform to said electrocardiographic data. As an option, said one or more baseline models are trained using clinical data and ECG databases to recognize when ECGs are of sufficient quality for interpretation, and to learn baseline heart rhythm/rate interpretation. As an option, the image processing model is configured to identify one or more ECG characteristics. As an option, said one or more ECG characteristics comprising: horizontal baseline, QRS, QT, and T-wave. As an option, the image processing model comprises image processing code block(s) optimized for a given ECG category. As an option, providing said QTc measurement to one or more machine learning models to generate a dose recommendation for a patient; and outputting the generated dose recommendation. As an option, the dose recommendation is validated based on a risk threshold associated with QTc for given a drug. As an option, generating a dosing recommendation based on said QTc measurement, wherein the computed QTc derived from QT. As an option, optimizing said one or more baseline models using one-shot architecture search. As an option, applying a generative adversarial network to generate synthetic data with artifacts for optimizing said one or more baseline models. As an option, applying the QTc measurement to guide drug dosing for remote drug initiation. As an option, applying the QTc measurement with a WCD device to provide remote AAD initiation; wherein the WCD or defibrillator device is configured to utilize pulse sensor data. As an option, the first module further comprises an interface configured to receive from the patient, through the secured communication, one or more inputs in relation to dosing of a ADD drug. As an option, wherein the interface is further configured to display said one or more inputs or store said one or more input for display at a time following the display. As an option, wherein said one or more inputs comprise personal information of the patient and a selection of drugs for dosing or a stage of dosing for a dosed drug. As an option, the interface is further configured to display a graphical representation of the QTc. As an option, wherein the QT segment is visually demarcated. As an option, the QTc is annotated with annotations that are automated measurements; the annotations are togglable. As an option, the first module is configured to perform safety checks based on cardiac physiology of the patient prior to dosing. As an option, wherein said one or more provided dosage recommendations are generated based on the QTc measurements. As an option, the system is configured to provide dosage recommendations by referencing the QTc measurements and one or more clinical metrics. As an option, the first module is configured to transmit patient-related input to and from a third-party application using the secured communication, the patient-related input is displayed to the patient. As an option, the first module is configured to transmit ECG data to and from a third-party application using the secured communication for determining the QTc measurements. As an option, the first module is configured to receive and transmit information to and from a third-party through the secured communication, wherein said information relates to said one or more dosage recommendations, a drug, and/or physical condition of a patient and/or psychological condition of a patient. As an option, the second module is configured to receive and process one or more user inputs, wherein said one or more user inputs are used for providing said one or more dosage recommendations in accordance with the QTc measurements.

Any reference to 'an' item refers to one or more of those items. The term 'comprising' is used herein to mean including the method steps or elements identified, but that such steps or elements do not comprise an exclusive list and a method or apparatus may contain additional steps or elements. As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary," "example," or "embodiment" is intended to mean "serving as an illustration or example of something." Further, to the extent that the term "includes" is used in either the detailed description or the claims, such a term is intended to be inclusive in a manner similar to the term "comprising" as "comprising" is interpreted when employed as a transitional word in a claim.

The figures illustrate exemplary methods. While the methods are shown and described as being a series of acts that are performed in a particular sequence, it is to be understood and appreciated that the methods are not limited by the order of the sequence. For example, some acts can occur in a different order than what is described herein. In addition, an act can occur concurrently with another act. Further, in some instances, not all acts may be required to implement a method described herein. Moreover, the acts described herein may comprise computer-executable instructions that can be implemented by one or more processors and/or stored on a computer-readable medium or media. The computer-executable instructions can include routines, subroutines, programs, threads of execution, and/or the like. Still further, results of acts of the methods can be stored in a computer-readable medium, displayed on a display device, and/or the like.

The invention claimed is:

1. An interactive remote drug dose guidance and physiologic response monitoring system for a patient, the system comprising:

a first module configured to interface with the patient using a secured communication, wherein the first module is adapted to receive periodically, through the secured communication, electrocardiogram (ECG) data from the patient for a predetermined time period until completion of a drug load;

a second module configured to generate one or more corrected QT interval (QTc) measurements based on the periodically received ECG data, wherein at least one of said one or more QTc measurements meets a threshold value; and a third module configured to provide said one or more dosage recommendations derived from said one or more QTc measurements generated by the second module, within the predetermined time period, with each dosage recommendation provided in a sequential manner based on said one or more QTc measurements, wherein each subsequent dosage recommendation is generated based on a corrected QT interval (QTc) measurement generated from ECG data subsequently received during the predetermined time period.

2. The system of claim 1, wherein the first module comprises an interface configured to receive from the patient, through the secured communication, one or more inputs in relation to dosing of a drug.

3. The system of claim 2, wherein said one or more inputs comprise personal information of the patient and a selection of drugs for dosing or a stage of dosing for a dosed drug.

4. The system of claim 2, wherein the interface is configured to display said one or more inputs or store said one or more input for display at a later time.

5. The system of claim 2, wherein the interface is configured to display a graphical representation of said one or more corrected QT interval (QTc) measurements.

6. The system of claim 5, wherein a QT segment of said one or more QTc measurements is visually demarcated on the graphical representation.

7. The system of claim 5, wherein each QTc measurement is annotated with annotations that are automated measurements and the annotations are togglable on the graphical representation.

8. The system of claim 1, wherein the first module is capable of performing safety checks based on cardiac physiology of the patient prior to dosing.

9. The system of claim 1, wherein the second module is configured to:

cleanse the received ECG data; extract ECG segments from cleansed electrocardiographic data based on ECG channel electrode(s) of interest; provide one or more baseline models trained with annotated segments to generate interpreted heart rhythm or rate based on the extracted ECG segments; select an image or signal processing model based on the interpreted heart rhythm or rate; and apply the selected image or signal processing model to the cleansed electrocardiographic data to generate said one or more QTc measurements.

10. The system of claim 9, wherein said one or more provided dosage recommendations are generated based on said one or more QTc measurements.

11. The system of claim 1, wherein the system is configured to provide dosage recommendations by referencing said one or more QTc measurements and one or more clinical metrics.

12. The system of claim 1, wherein the first module is configured to transmit patient-related input to and from a third-party application using the secured communication.

13. The system of claim 12, wherein the patient-related input is displayed to the patient.

14. The system of claim 1, wherein the first module is configured to transmit ECG data to and from a third-party application using the secured communication for determining said one or more QTc measurements.

15. The system of claim 1, wherein the first module is configured to receive and transmit information to and from a third party through the secured communication, wherein said information relates to said one or more dosage recommendations, a drug, and/or physical or psychological condition of a patient.

16. The system of claim 1, wherein the second module is configured to receive and process one or more user inputs, wherein said one or more user inputs are used for providing said one or more dosage recommendations in accordance with said one or more QTc measurements.

17. The system of claim 1, further comprising: a selection module configured to select an ECG lead using one or more machine learning (ML) models.

18. The system of claim 17, wherein the selection module is further configured to select, from the ECG data, data that are associated with a preferred heartbeat displayed on the interface for approval.

19. A computer-implemented method of providing remote antiarrhythmic drug (AAD) initiation using a defibrillator device, the method comprising:

receiving electrocardiogram at least one electrocardiogram (ECG) source; cleansing said electrocardiographic data;

extracting ECG segments from cleansed electrocardiographic data based on ECG channel electrode(s) of interest; providing one or more baseline models trained with annotated segments to generate interpreted heart rhythm or rate based on the extracted ECG segments;

selecting an image processing model based on the interpreted heart rhythm or rate;

applying the selected image processing model to the cleansed electrocardiographic data, wherein the image processing model outputs a corrected QT interval (QTc) measurement, wherein the corrected QTc measurement meets a threshold value; and applying the QTc measurement with the defibrillator device to provide the remote AAD initiation, wherein the defibrillator is configured to utilize pulse sensor data to distinguish between perfusing and pulseless ventricular arrhythmias in relation to the QTc measurement, wherein remote AAD initiation is further based on a subsequent corrected QT interval (QTc) measurement generated from subsequently received electrocardiographic data.

20. A system for clinical decision-making using a mobile cardiac telemetry (MCT) device, the system comprising:

one or more modules configured to interface with a patient via a secured communication, wherein said one or more modules are adapted to receive, through the secured communication, electrocardiogram (ECG) telemetry data from the patient for a predetermined time period until a clinical decision is made, and wherein said one or more modules are further configured to exhibit arrhythmia information to an interface based on input from the MCT device, wherein the MCT device is adapted to provide the arrhythmia information in accordance with the clinical decision; and another module of said one or more modules configured to generate one or more corrected QT interval (QTc) measurements, at least one QTc measurement meets a threshold value, based on the received ECG data and arrhythmia information to provide clinical decision-making based on said one or more QTc measurements within the predetermined time period, wherein the clinical decision-making is further based on a subsequent corrected QT interval (QTc) measurement generated during the predetermined time period.

* * * * *